(12) United States Patent
Van Ginneken (10) Patent No.: US 11,865,319 B2
(45) Date of Patent: Jan. 9, 2024

(54) CONTAINER WHICH CAN BE PREFILLED OR IS PREFILLED WITH FLUID, AS WELL AS A CANNULA ASSEMBLY AND CLOSURE SYSTEM FOR A CONTAINER WHICH CAN BE PREFILLED OR IS PREFILLED WITH FLUID

(71) Applicant: Schott Pharma Schweiz AG, St. Gallen (CH)

(72) Inventor: Tom Van Ginneken, Rorschacherberg (CH)

(73) Assignee: Schott Pharma Schweiz AG, St. Gallen (CH)

( * ) Notice: Subject to any disclaimer, the term of this patent is extended or adjusted under 35 U.S.C. 154(b) by 592 days.

(21) Appl. No.: 16/899,953

(22) Filed: Jun. 12, 2020

(65) Prior Publication Data

US 2020/0390978 A1 Dec. 17, 2020

(30) Foreign Application Priority Data

Jun. 13, 2019 (EP) ..................................... 19180053

(51) Int. Cl.
*A61M 5/32* (2006.01)
*A61J 1/14* (2023.01)
(Continued)

(52) U.S. Cl.
CPC ......... *A61M 5/3202* (2013.01); *A61F 9/0008* (2013.01); *A61J 1/1468* (2015.05); *A61J 7/0053* (2013.01); *A61K 31/728* (2013.01); *A61K 38/4893* (2013.01); *A61M 5/007* (2013.01); *A61M 5/28* (2013.01); *A61M 5/329* (2013.01); *A61M 5/343* (2013.01); *A61M 5/347* (2013.01); *A61M 2005/3109* (2013.01)

(58) Field of Classification Search
CPC ................ A61M 5/3202; A61M 5/343; A61M 2005/3109
See application file for complete search history.

(56) References Cited

U.S. PATENT DOCUMENTS 2,034,294 A 3/1936 Hein
6,485,474 B1 * 11/2002 Heinz ................. A61M 5/3202
604/199

(Continued)

FOREIGN PATENT DOCUMENTS

CH 583 567 1/1977
DE 27 17 830 A1 11/1977
(Continued)

*Primary Examiner* — Bradley J Osinski
(74) *Attorney, Agent, or Firm* — Taylor IP, P.C.

(57) ABSTRACT

A pre-Tillable or prefilled container for at least one of storage or application of a fluid includes: a receptacle having a chamber for accommodation of the fluid; a cannula assembly including a cannula and a sealing element, the cannula having an outside channel opening, the cannula assembly being attachable to the receptacle; and a closure cap including a sealing. The channel opening of the cannula protrudes into the sealing of the closure cap thus sealing the channel opening. Due to at least one of a radial compression or an axial compression of the sealing element, as well as due to sealing of the channel opening by the closure cap, the chamber is sealed in a fluid-tight manner.

20 Claims, 4 Drawing Sheets

(51) Int. Cl.
*A61F 9/00* (2006.01)
*A61J 7/00* (2006.01)
*A61K 31/728* (2006.01)
*A61K 38/48* (2006.01)
*A61M 5/00* (2006.01)
*A61M 5/28* (2006.01)
*A61M 5/34* (2006.01)
*A61M 5/31* (2006.01)

(56) References Cited

U.S. PATENT DOCUMENTS

| | | | |
|---|---|---|---|
| 6,488,666 B1 | 12/2002 | Geist | |
| 10,022,504 B2 * | 7/2018 | Horvath | A61M 5/344 |
| 2006/0052747 A1 * | 3/2006 | Nishimura | A61M 5/31596 |
| | | | 604/86 |
| 2008/0228161 A1 * | 9/2008 | Claussen | A61M 5/14 |
| | | | 604/404 |
| 2013/0303995 A1 * | 11/2013 | Tachikawa | A61M 5/344 |
| | | | 604/240 |
| 2018/0257975 A1 * | 9/2018 | Kimura | C03B 23/09 |

FOREIGN PATENT DOCUMENTS

| | | |
|---|---|---|
| DE | 10 2014 007 604 A1 | 11/2015 |
| DE | 10 2014 211 018 A1 | 12/2015 |
| EP | 1 364 670 A2 | 11/2003 |
| GB | 377891 | 8/1932 |
| WO | 02/087671 A1 | 11/2002 |

* cited by examiner

FIG. 6 ated CONTAINER WHICH CAN BE PREFILLED OR IS PREFILLED WITH FLUID, AS WELL AS A CANNULA ASSEMBLY AND CLOSURE SYSTEM FOR A CONTAINER WHICH CAN BE PREFILLED OR IS PREFILLED WITH FLUID

CROSS REFERENCE TO RELATED APPLICATIONS

This application claims priority to European Patent Application EP 19 180 053.1, filed Jun. 13, 2019, which is incorporated in its entirety herein by reference.

BACKGROUND OF THE INVENTION

1. Field of the Invention

The present invention relates to a container which can be prefilled or is prefilled with a fluid, in particular with a pharmaceutical or cosmetic preparation, a cannula assembly and a closure system for a container which can be prefilled or is prefilled with a fluid, in particular with a pharmaceutical or cosmetic preparation. The container can include a syringe or cartridge, a syringe body or an injection device.

The fluid, in particular the pharmaceutical or cosmetic preparation, can be stored in the container and/or can be injected or administered the container. Overall, in the case of a prefilled syringe, injections are in the foreground as applications, however, with the subject of the present invention, fluid can also be removed. Such systems may for example also be used for dispensing, for example for an infusion. Moreover, the application can, but does not have to include penetration of the human or animal body, but may also include applying, for example, drops of an anesthetic onto a body region of a patient, as is the case many times for example for local anesthesia in oral surgery prior to injecting an anesthetic.

The designation "medical preparation" within the scope of the present invention also includes veterinary medical preparations and their appropriate use.

2. Description of the Related Art

Appropriate storage as well as correct application of preparations, such as the previously described medical, pharmaceutical, cosmetic, and/or veterinary medical preparations, is generally of great importance; in particular, the sterility during the entire storage time is of great importance.

The containers for cosmetic or pharmaceutical preparations, for example syringes or cartridges discussed within the scope of the present disclosure also make a significant contribution in regard to administering these preparations. These generally cylindrical containers typically include a chamber for accommodation of the preparation, the chamber being limited by a proximal and a distal end.

Within the framework of the present disclosure, the proximal end is understood to always be the end into which a stopper or plunger is inserted, whereas the distal end is understood to be the end to which, for example, a cannula together with its cannula assembly can be attached. In regard to a common description in relevant professional literature, the end facing toward the user during normal handling is described as proximal end and the end facing away from the user and facing toward the patient during application of cosmetic and/or medical preparations is described as distal end.

Insofar these terms "proximal" and "distal" are used for various assemblies the previously explained geometric conditions are herein always disclosed in the same manner for the respective assembly.

During a typical application of the pharmaceutical or cosmetic preparation, the proximal end will thus be facing toward a user and the distal end will be facing away from the user.

A plunger can, in particular, be inserted into the proximal end in order to move the preparation, in particular in a sliding motion, in the distal direction and through a through-channel at the distal end of the container; or in reverse direction to draw a preparation or also a bodily fluid of a patient through said opening into the container, in particular into the syringe. The end piece of the container surrounding the through channel is therein often, at least in sections, designed with a conically tapering tip or cone.

For injecting or applying a preparation, a cannula can be attached to this cone, as described, for example, in publication GB 377,891. The therein described placement onto the cone allows for simple replacement of the cannula. U.S. Pat. No. 2,034,294 describes a similar principle of connecting a cannula with a cone with a syringe.

Another embodiment for connecting a cannula with a syringe is described in publication WO 02/087671 A1. In order to prevent hazards which are inherent with a cannula which is permanently mounted on a syringe—for example transmission of illnesses through contact with a used cannula—a system is suggested where the cannula is retractable into the chamber of the container after administering of the preparation. The entire cannula is therein drawn into the chamber through retracting of the plunger.

For faster and easier administering of pharmaceutical preparations, already prefilled syringes or cartridges are currently used more and more frequently. This eliminates transfer of the active substance from a first reservoir into the chamber of the container prior to being administered which, on the one hand, shortens the time required for the application, and on the other hand, also helps to avoid losses due to transfer of preparation. This is particularly advantageous in the case of high-grade medications. Moreover, the danger of contamination of the active substances and of infection can also be reduced.

For this purpose, plastic containers are known in the medical field, which are equipped with a closure and which are described, for Example, in publication DE 10 2014 007 604 A1. Prefilled containers can be sealed with the closure, wherein the closure is then opened when administering the preparation and a cannula can instead be attached.

An additional container is described, for example, in DE 10 2014 211 018 A1. The container described in said publication consists of glass in order to advantageously exploit the inert characteristics of the glass in regard to expensive, highly effective medications. An opening in the glass container is sealed with a plastic connecting element which seals the container chamber and the outlet of a preparation inside said container. For later application of the preparation that is filled in the container, the connecting element is opened, and the container is connected with a cannula at this point, by which the preparation can subsequently be administered.

In this manner, prefilled syringes can be produced, however the application of the preparation is still subject to a certain effort since the container chamber must be opened prior to each application. In addition, a suitable cannula must be found and must also be opened and must be connected with the prefilled syringe. In addition to the increased time requirement, this change also carries with it a certain risk of contamination if, for example, the opened cannula comes into contact with an undesirable substance before the cannula is attached to the syringe.

Moreover, disposable syringes are known with ready to use medication filling. For example, in publication DE 27 17 830 A1, a prefilled disposable syringe is described which is already fitted with a cannula.

Publication EP 1 364 670 A3 also describes a disposable syringe with a cannula in a needle channel of the syringe.

With this type of disposable syringe, the cannula is initially connected with the container body. The syringe is then filled with the pharmaceutical preparation. In the case of plastic containers, the cannula is often already attached to the container during production of same which typically occurs in an injection molding process, that is to say the cannula is overmolded with injection molding material and is thus connected with the container in a material-sealed manner. This is, however, inconvenient since for each geometry of cannula or container appropriate injection tools have to be provided.

This also means that, during the manufacturing process, the container body has to be moved together with the cannula, which requires special care in their respective handling.

An additional significant disadvantage is that cannulas with a relatively small diameter cannot regularly be connected with the container body in the injection molding process. A common size identification of the cannula in regard to its outside diameter is the size being specified in gauge (G). Cannulas having an outside diameter of greater than 30 G, that is to say 31 G, 32 G, 33 G or 34 G, cannot routinely be produced in the injection molding process. Thus, no prefilled disposable syringes with ready for use medication filling can be provided with such thin cannulas, in particular with such having a size between 31 G to 34 G. This is disadvantageous insofar as, for example, the sensation of pain decreases with a smaller outside diameter of the cannula when injecting a pharmaceutical preparation into the human body, which is why, if possible, cannulas with a small outside diameter are used.

In addition, the wide variety which can result, for example, in regard to the size of the chamber for the preparation in conjunction with different dimensions of the cannula becomes quickly increases rapidly and can lead to a high number of tools required for the production and expensive storage.

The cannula is often also glued into the channel of the syringe. This is generally viewed as being disadvantageous, since herein an additional material is used which can lead to undesired contamination of the prefilled preparation, in particular over a longer time period, for example of more than one year to more than 3 years. Also disadvantageous in this case could be a possible contamination of the pharmaceutical preparation due to outgassing of or from the used adhesive. This could, for example, contaminate and damage the prefilled medication. Since such a contamination may not be visible to the user, this should be avoided with especially high reliability.

What is needed in the art is a pre-Tillable container for pharmaceutical preparations, which can be filled with a fluid, in particular a pharmaceutical or cosmetic preparation and with which an application or injection of said fluid from, or respectively with the prefilled container is possible, without removal of a closure and/or attachment of a cannula or another component becoming necessary.

SUMMARY OF THE INVENTION

In some exemplary embodiments provided according to the present invention, a pre-Tillable or prefilled container for at least one of storage or application of a fluid includes: a receptacle having a chamber for accommodation of the fluid; a cannula assembly including a cannula and a sealing element, the cannula having an outside channel opening, the cannula assembly being attachable to the receptacle; and a closure cap including a sealing. The channel opening of the cannula protrudes into the sealing of the closure cap thus sealing the channel opening. Due to at least one of a radial compression or an axial compression of the sealing element, as well as due to sealing of the channel opening by the closure cap, the chamber is sealed in a fluid-tight manner.

In some exemplary embodiments provided according to the present invention, a closure system for connecting a cannula with a receptacle includes a cannula assembly. The cannula assembly includes: a cylindrically symmetric sealing element with an axial passage; and a cannula arranged coaxially relative to the sealing element and at least in sections inside the axial passage of the sealing element. One section of an outside surface area of the cannula is connected firmly with the sealing element in at least one of a material seal or a form fitting manner and at least one face side of the sealing element includes a circular region surrounding the passage. The region forms a face-side sealing surface in a plane vertical to a center axis of the sealing element.

In some exemplary embodiments provided according to the present invention, a method of treating a patient includes injecting or applying a medical preparation to the patient. The medical preparation is held in a container. The container includes: a receptacle having a chamber for accommodation of the fluid; a cannula assembly including a cannula and a sealing element, the cannula having an outside channel opening, the cannula assembly being attachable to the receptacle; and a closure cap including a sealing. The channel opening of the cannula protrudes into the sealing of the closure cap thus sealing the channel opening. Due to at least one of a radial compression or an axial compression of the sealing element, as well as due to sealing of the channel opening by the closure cap, the chamber is sealed in a fluid-tight manner.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Exemplary embodiments provided according to the present invention provide a pre-fillable container for pharmaceutical preparations, which can be filled with a fluid, in particular a pharmaceutical or cosmetic preparation and with which an application or injection of said fluid from, or respectively with the prefilled container is possible, without removal of a closure and/or attachment of a cannula or another component becoming necessary.

The container, prefilled with the fluid, can offer improved storage capability of at least one year, such as of at least two years, of at least three years or even longer. The container, prefilled with the fluid—in particular in cases where the fluid is a pharmaceutical or cosmetic preparation can meet the current sterilization requirements for the pharmaceutical sector over said time period, especially those pertaining to storage of pharmaceutical preparations.

As far as possible, one can rely herein on existing geometries of receptacles, in particular syringes, syringe bodies, cartridges or injection devices, and cannulas which are currently on the market.

Exemplary embodiments disclosed herein thus provide a container for storage and application of a fluid, in particular of a pharmaceutical or cosmetic preparation. The container can be stored over an extended time period and which in regard to the dimensions of the receptacles and the cannula is flexible, and which is preassembled or can be preassembled and which is prefilled or can be prefilled.

The pre-fillable or prefilled container can therein be equipped with very thin cannulas, in particular also with cannulas having a gauge size between 31 G to 34 G.

In addition, a prefilled container can have a storage capability of at least three years. The current sterilization requirements for storage of fluids, in particular storage of pharmaceutical or cosmetic preparations, can be adhered to.

Moreover, modular receptacles and cannulas available on the market are able to be used.

According to the present invention, a pre-fillable or pre-filled container for storage and/or application of a fluid, in particular a pharmaceutical or cosmetic preparation is provided, including a receptacle, such as a syringe having a syringe body, a cannula, or an injection device, with a chamber for accommodation of the fluid, also including a cannula assembly including a cannula and a sealing element and the cannula assembly can be attached to the receptacle, as well as comprising a closure cap. An outside channel opening of the cannula protrudes into a sealing, such as elastomer internal region of the closure cap, thus sealing the channel opening. Due to a radial and/or axial compression of the sealing element, as well as due to sealing of the channel opening by the closure cap, the chamber is sealed in a fluid-tight manner.

The facilitated storage time in regard to stability and sterility of more than three years is achieved in particular through the axial and/or radial compression of the sealing element of the cannula assembly, and by sealing of the cannula by the closure cap. At least two sealing areas are defined: the sealing surface of the sealing element toward a front region or distal end of the receptacle, which may be in the embodiment of a Luer-Lock, and the seal in the closure cap of the cannula, which seals the outside channel opening of the cannula.

This results advantageously in the use of a prefilled container as disclosed herein, for sterile storage of a pharmaceutical or cosmetic preparation over a storage period of more than one, such as more than two years or more than three years.

The term "prefilled container" describes herein a filled container which does not need to be filled by the respective user but which was already filled, for example, by the manufacturer of the respective preparation or in subsequent processing—for example by additional fill- or active substances—by the respective processor or filler.

However, the subsequent users can themselves also prefill the container disclosed herein, for example, in a clinical environment, in order to store it, for example, over a longer time period so that it becomes instantly available, particularly in time-critical situations as can occur, for example, in emergency health care. Preparations for use in time-critical or emergency health care situations can herewith be stored over longer periods and the regular replacement thereof due to the expiration date of the specific preparation can be clearly reduced.

"Sterile storage" is herein understood to be a storage which meets the necessary sterility conditions over a specified time period. The requirement for such sterility conditions is typically such that, after sterilization, a prefilled container as disclosed herein has a population in its interior of living individuals, for example germs or micro organisms, of less than $10^{-6}$ times which, in their number, are thus reduced to less than one millionth. Storage which meets these conditions over the respectively specified time period is regarded as "sterile storage" for this time period. Sterilization methods are extensively known to the expert and will be discussed again further herein.

The cannula assembly and the adapter serve to firmly and permanently connect a cannula with a receptacle, such as a syringe, a syringe body, a cartridge or an injection device and thereby seal the opening at the distal end, in order to create a pre-fillable container for storage and application of a fluid, in particular a pharmaceutical or cosmetic preparation. A pre-fillable or prefilled container provided according to the present invention therefore includes at least one such a receptacle and a cannula attached to the receptacle.

For accommodation of the fluid, the receptacle can have a chamber which is filled, or can be filled, with the fluid. The fluid can include a pharmaceutical or cosmetic preparation. It can include liquids, gases, solids, or mixtures thereof. A container which is prefilled with a fluid can be stored over an extended period prior to the fluid being administered by the cannula.

It is useful if removal of a closure and/or installation of a cannula or another component prior to an application becomes unnecessary. The present invention makes it possible to fill the receptacle with a fluid and to—before or afterwards—connect a cannula with this receptacle firmly and permanently, thus sealing the opening at the distal end. A prefilled container can be stored over an extended time period and can then be made available "ready to use" for application of the fluid, for example a pharmaceutical or cosmetic preparation.

The production process is comparatively simple since the cannula does not need to be attached during the time of fabrication of the receptacle.

According to the present invention, receptacles, such as syringes, syringe bodies, cartridges or injection devices and cannulas available on the market can be used. This simplifies availability insofar as these receptacles and cannulas can be combined with each other in many ways, thereby being able to show in a modular manner a wide spectrum of receptacles and cannulas for the pre-fillable or prefilled container.

This moreover results in that the number of devices and tools, for example the number of injection tools, can be significantly reduced.

Thus, components available on the market can be combined into a premanufactured unit as desired. Exemplary embodiments provided according to the present invention herewith offer the advantage of a cost reduction, in particular in regard to the devices and tools and at the same times offers high diversity in format and cannulas.

Moreover, additional components, for example adhesives in the contact area with the fluid, can be dispensed with, thereby improving the storage capability, since an undesired contamination of the fluid with components or reaction products of the adhesive can be avoided. The danger of a contamination of the fluid through outgassing from the adhesive can also be avoided, which is vitally important, in particular, in the case of pharmaceutical or cosmetic preparations.

One advantage of exemplary embodiments provided according to the present invention is that the connection between cannula and receptacle can be designed to be, in particular, impervious to fluid and gas. The tightness of the connection can, for example, be verified by helium overpressure process according to DIN EN 1779. The chamber of the container can herein be supplied with helium or a helium-containing gaseous mixture, closed and put under pressure. On the outside of the container, a leakage can then be detected by using an appropriate leakage detector. The liquid and gas tight formation of the connection between cannula and receptacle can be checked and verified by such a test.

Exemplary embodiments provided according to the present invention make it possible to create a connection between cannula and receptacle that is tight during pressurization up to 2 bar, or to 3 bar or higher. The connection between cannula and receptacle can thus be classified as being microbiologically tightly sealed. Consequently, the design of the connection between cannula and receptacle represents a sterility barrier which makes a long term storage capability possible.

This leads to the advantage of exemplary embodiments provided according to the present invention in that a container, prefilled with a fluid, for example a pharmaceutical or cosmetic preparation, after filling and sterilization can be stored for at least one year, such as at least two years, at least three years, or more than three years without the stability and sterility of the fluid, for example a pharmaceutical or cosmetic preparation, becoming unacceptably compromised.

The production of a prefilled container provided according to the present invention, including a receptacle and cannula, can occur as follows: The required components are produced and assembled under clean room conditions, are then sterilized and packaged in a sterile manner. This pre-fillable container can then be aseptically filled with the fluid, for example a pharmaceutical or cosmetic preparation, in order to thus provide the prefilled container.

It is also possible to fill a pre-fillable container in the clean room with the fluid, in particular with the pharmaceutical fluid, and to subsequently sterilize the prefilled container.

To administer pharmaceutical or cosmetic preparations, receptacles such as syringes, syringe bodies, cartridges or injection devices which are suitable according to the present invention are known and available in various sizes in the medical sector. Such receptacles are generally of a cylindrical, longitudinal shape and have a central chamber to accommodate the fluid. The chamber is limited axially by a proximal and a distal end. The distal end is understood to be the end of the chamber which, when administering the fluid faces away from the hand of the person operating the device.

The proximal end of the chamber typically includes an opening into which a stopper can be inserted to move a filled fluid by a stopper movement, for instance via a piston rod, driven hydraulically or by a pump in an axial direction toward the opposite distal end, which typically includes a tip with a through-channel to the chamber. An important element herein is the insertion of the stopper which is then moved either with a piston rod or, for example, hydraulically in direction of the cannula, for example, to deliver a medication. The tip may be graduated, reduced, or conically tapered.

With a relevant stopper movement, the fluid can then be removed through this through-channel inside the generally graduated tip. The central axis of the container represents the longitudinal axis of the arrangement described further herein.

If reference is made subsequently to an "application," this is to be understood on the one hand to be injecting of a fluid, for example a pharmaceutical or cosmetic preparation by a prefilled or filled container. Application includes thereby, for example, injecting of cosmetic or pharmaceutical preparation from the prefilled container into the human body.

It is however also possible to use a pre-fillable container according to the present invention for removal or accommodation of a fluid. In this case, the term "application" refers to accommodation of a fluid in the chamber.

"Application" further includes use of the container for dispensing, for example in the context of an infusion. In summary, during an application, a fluid enters into the chamber through the through-channel or leaves the chamber through the through-channel.

According to the present invention, a cannula assembly and an adapter are provided to connect the cannula with the receptacle.

In some exemplary embodiments provided according to the present invention, a cannula assembly includes a cylindrically symmetric sealing element with an axial passage and a cannula, the cannula being arranged coaxially relative to the sealing element and at least in sections inside the central passage of the sealing element. One section of an outside surface area of the cannula is connected firmly with the sealing element in a material seal and/or form fitting manner and at least one face of the sealing element includes a circular region surrounding the passage. The region forms a face-side sealing surface in a plane vertical to the center axis of the sealing element.

Insofar as a material seal and/or form-fit connection is referenced within the scope of the present invention, the term "material seal" means a cohesion of the connective partner elements by atomic or molecular forces. The term "form-fit" indicates locking of at least two connective partners.

The cylindrically symmetric sealing element is designed with an axially central passage. This serves to accommodate the cannula.

In the following, a cannula is understood to be a hollow needle or an injection needle with a through-channel which can be used, for example, in the medical sector.

The outside diameter of the cannula is stated typically in the size identification of gauge and is recorded in the relevant standards EN ISO 6009 and EN ISO 9626. According to the present invention, cannulas having a gauge size from 10 G to 34 G, or even a lesser outside diameter, can be used. Common gauge sizes which can be assembled either by adhesion or in injection molding are 10 G to 29 G.

Cannulas having a smaller outside diameter are more advantageous in a patient-friendly application of a pharmaceutical preparation. Thus the present invention makes the use of cannula sizes 27 G to 30 G, such as 31 G, 32 G, 33 G, and 34 G and above, where possible.

According to the present invention, the cannula can be arranged coaxially relative to the sealing element in such a way that, in an assembled position, the cannula is arranged at least sectionally inside the central passage of the sealing element. The sealing element and the cannula may be connected firmly and closely with one another. The connection between cannula and sealing element may be designed to be impervious to liquid and/or gas.

The cannula assembly can be fitted on the tip of the receptacle in order to position the cannula radially and/or axially relative to the through-channel of the receptacle.

In its fitted position, the cannula assembly can moreover ensure the necessary seal for the through-channel of the receptacle. To secure the cannula assembly on the tip of the receptacle and to produce the sealing effect, the sealing element is subjected in its mounted position to an axial contact pressure and pressed in the direction of the tip. According to the present invention, an adapter is provided for this.

The liquid- and/or gas tight seal of the through-channel of the receptacle occurs on the one hand by the previously discussed liquid- and/or gas tight design of the connection between the sealing element and cannula which prevents passing of fluid or other substances between sealing element and cannula, and on the other hand by the face-side pressing the sealing element onto the tip surrounding the through-channel.

In this way, the sterility requirements for pharmaceutical or cosmetic preparations can be met when they have been filled into the chamber, since intrusion of alien substances such as gases, germs, or others into the chamber can be prevented.

The cannula can be held in the passage of the sealing element, for example, by clamping and/or friction, that is to say the inside diameter of the passage of the sealing element can feature an undersize relative to the outside diameter of the cannula in the section that is intended for fastening with the sealing element. The inside diameter of the passage of the sealing element can thus be adapted to the outside diameter of the cannula.

Alternatively or in addition to clamping, the cannula can be materially connected with the sealing element with a connecting point or a connecting surface, for example by laser welding. Due to the firm connection, a connecting surface is useful which can be formed by a section of the outside surface of the cannula, with an appropriate section of the inside wall of the passage.

Supplementary or in addition, the cannula can also have a protrusion on the outside surface, for example in the embodiment of a peripheral fin which, in an assembled state, can engage with a precisely fitting opposite recess or groove, such as inside the passage of the sealing element, thus being able to counter even more effectively an axial movement of the sealing element retained in the cannula.

In some embodiments, the cannula completely penetrates the passage of the sealing element. Herein it can be useful that the cannula is flush with the sealing element, at least at the location which in an assembled state faces toward the chamber. During use, this has the advantage that, when completely emptied, the dead volume in the chamber can be kept as low as possible. A small protrusion of the cannula opposite sealing element on the side which, in the assembled position, faces toward the direction of the chamber can, on the other hand, support that the chamber and the cannula can flawlessly communicate with one another and that therefore a fluid from the chamber can enter into the cannula without the danger that the cannula entrance is covered by the sealing element. A protrusion of the cannula of approximately 0.1 mm to 3 mm, such as to 2 mm respective to the face-side sealing surface which, in assembled position, points toward the chamber is thus advantageous.

The protrusion of the canula on the opposite side of the sealing element provides the necessary clearance of the cannula relative to the receptacle which is necessary for applying the fluid when using the container. This free length of the needle may be in a range of approximately 0.6 cm (⅜ inch) to approximately 5 cm (2 inch).

The sealing element may be manufactured from an elastomer material. Such materials have a certain flexibility or respectively compressibility under compressive stress and are thus suitable for sealing of openings. The sealing element can thus be attached to the through-channel on the tip of the receptacle and can be pressed on axially in order to seal the opening. Thus, when the cannula assembly is mounted on the container, the sealing element can firmly and permanently close the clearance which occurs between the outside surface of a cannula protruding into or respectively adjoining the through-channel, and the inside wall of the through-channel in the region of the syringe.

Since in this way, the sealing element can come into contact with a fluid filled into the chamber, for example contact with a therein filled pharmaceutical or cosmetic preparation, it is advantageous if the elastomer material of the sealing element is permissible for use in contact with a pharmaceutical preparation. In this manner, contamination of a filled fluid can be countered, so that a long durability and shelf life of a fluid filled into the chamber is provided. Suitable elastomer materials can, for example, be a thermoplastic elastomer, in particular butyl-, chloro-butyl-, bromobutyl- or polyisoprene rubber.

In order to be able to especially effectively seal the typically tapered tip of the receptacle it is advantageous if at least one face of the sealing element includes a circular region surrounding the passage of the sealing element, whereby the region forms a sealing surface in a plane vertical to the center axis of the sealing element. This face-side sealing surface can be flat, but however does not have to be and can, for example, be conically elongated toward the center. This sealing surface may be located on the side which, in the assembled position, points toward the container and is in contact with the face of the container or respectively with the face of the tip, in order to seal same. The sealing surface thus represents a limit stop.

The geometric design of the surface of the face-side sealing surface may thereby be adapted to the shape of the face of the tip that is to be sealed. If, for example, the face side of the tip which is to be sealed is in the embodiment of a flat circular surface, it would be appropriate to also design the sealing surface of the sealing element flat. If, for example, the face side of the tip which is to be sealed is designed with a sealing surface conically elongated toward the center, a diametrically opposed design of sealing surface of the sealing element—for example, a concave shape—can be useful.

In the assembled position, the face-side sealing surface of the sealing element therefore forms a circumferential contact and sealing surface with the face side of the tip, and may lay flat, circumferentially on the face surface of the tip and can in addition protrude into the gap between cannula and inside wall, thus increasing the sealing effect.

In the assembled state, the cannula can communicate with the chamber of the container. This means that a fluid can be moved from the chamber into the cannula, or also vice versa. In an assembled state, the cannula can protrude to a lesser extent into the through-channel of the tip of the container, and the free space forming between the cannula and the through-channel is being sealed by the sealing element, in the face region of the tip.

To be able to seal the free space, the inside and outside diameter of the sealing element which limit the sealing area outside and inside are adapted geometrically to the face side of the container or respectively the tip with which they are in contact in an assembled state.

To ensure full surface sealing, the circular shaped sealing area may measure in the radial direction at least 0.5 mm, such as at least 0.7 mm or at least 1 mm. In some embodiments, the circular sealing area has a spread in the radial direction which is consistent at least with the radial expansion of the face-side surface of the tip. A slight radial overlap of the face-side surface by the circular sealing area toward inside and/or outside can be advantageous in an assembled state in order to create an as wide as possible sealing area as contact surface between sealing element and tip.

It is advantageous if the inside diameter of the passage of the sealing element is smaller, or at least not larger, than the inside diameter of the through-channel of the receptacle, where the inside diameter of the passage of the sealing element ultimately conforms to the gauge size of the cannula.

It is moreover advantageous if the outside diameter of the sealing element is designed corresponding to the outside diameter of the tip, in order to avoid a protrusion relative to the tip.

Common sizes of suitable receptacles and tips are specified in Standard ISO 80369-7.

To further increase the sealing effect, the face-side sealing area can be designed alternatively, or in addition, with a central, truncated cone shaped protrusion. This can surround the central passage of the sealing element and, in an assembled state, can engage with or respectively protrude at least in its face-side region into the through-channel of the tip. In this way, an additional seal can be created conveniently between tip and sealing element, where the advantage occurs in that the seal between the sealing element and through-channel occurs already in the through-channel so that no fluid can get into the gap between the face sides of tip and sealing element. The protrusion allows also better guidance and/or positioning of the cannula in the through-channel and/or relative to the receptacle.

The truncated cone shaped protrusion can also be advantageously adapted geometrically to the through-channel of the container that is to be closed. It has turned out advantageously if its length in axial direction is such that, in an assembled position, the protrusion protrudes into the through-channel at least 0.1 mm, such as at least 1 mm or at least 2 mm, and not more than 5 mm, such as not more than 4 mm or not more than 3 mm.

To achieve an efficient sealing effect, the angle between the axis of the truncated cone shaped protrusion and the outside surface line is at least 1°, such as at least 8° or at least 10° to 30°.

Also advantageous herein is the self-alignment during assembly of cannula assembly and receptable.

The intent of some exemplary embodiments provided according to the present invention is to connect the cannula assembly, including the cannula and sealing element, firmly and permanently with the tip of the receptacle, in particular a syringe, a syringe body, a cartridge or an injection device, in order to provide the pre-fillable and/or prefilled container for storage and/or application of a fluid, for example a pharmaceutical or cosmetic preparation.

In some embodiments, an adapter is suggested for firm and permanent sealed connection of a cannula, in particular a cannular assembly, with the tip of a receptacle, in particular a syringe, a syringe body, a cartridge or an injection device. By using this adapter, it is possible to connect a cannula firmly and permanently sealed with the receptacle in such a way that the aforementioned demands, in particular in regard to the storage capability and/or the sterility requirements, can be adhered to.

The adapter provided according to the present invention facilitates in an especially simple manner provision of axial and/or radial compression, which is required in order to connect the cannula assembly firmly and permanently sealed with the receptacle.

In order to be able to fill, close and open again, such receptacles, in particular a syringe, a syringe body, a cartridge or an injection device, connecting systems have been developed for the medical sector which are based on a so-called Luer-Lock connection. Receptacles are available for storage and administering of pharmaceutical preparations which are equipped with a first part of a Luer-Luck connection and which, by a closure comprising a second part of a Luer-Lock connection, can be closed and at a later date can be opened for administering a preparation. This type of connection based on the Luer-Lock principle may be advantageously used according to the present invention.

A Luer-Lock connection includes a connecting element with an inside thread as a first part of the Luer-Lock connection into which a second connecting element with an outside thread engages and can be secured with a turning motion around an axis of rotation. The connecting element having the inside thread is described as the male component of a Luer-Lock connection and the connecting element having the outside thread is described as the female component of the Luer-Lock connection.

It has been found that such a connecting principle for closing and opening a container is also particularly suitable for connecting the cannula with the container.

Exemplary embodiments disclosed herein thus provide an adapter for connecting a cannula, in particular a cannula assembly with a container, in particular with the tip of a receptacle such as a syringe, a syringe body, a cartridge or an injection device. The adapter is in the embodiment of an elongated hollow body with an axial passage opening, one proximal end and one distal end. An inside diameter of the passage opening is expanded at the proximal end and represents a retainer for holding the sealing element, and the proximal end includes an outside thread as part of a Luer-Lock connection which is or can be connected with the inside thread of the receptacle.

The terms "proximal" and "distal" herein define those face sides of the adapter which, in an assembled position, correspond to those of the receptacle, that is to say, for example, the syringe. In an assembled position, the proximal end of the adapter points for example toward the user.

The axial passage opening is therefore designed having at least two different inside diameters, where the section of the expanded inside diameter opens toward the side of the adapter which, in an assembled position, points toward the receptacle.

This expanded inside diameter may be advantageously geometrically adapted to the outside diameter of the sealing element of the cannula assembly that is to be incorporated and thereby make it possible to slide the sealing element of the cannula assembly at least partially, originating from the face side axially into the adapter until a limit stop which is formed by the transition of the passage opening with the expanded diameter to the passage opening with the smaller diameter and which thereby prevents further insertion of the sealing element.

The smaller inside diameter is selected such that, in an assembled position, the cannula can penetrate the passage opening in this region, whereas in contrast the sealing element is held in the intended position.

Alternatively, or in addition, an additional form-fitting connection can be created; that is to say, a connection caused by interlocking of at least two connecting partners between the inside wall of the passage and the sealing element, for example, by a peripheral groove which can be sized such that, in an assembled state, an outside section of the sealing element can engage with this groove. In this way, the sealing element can be retained in the adapter such that an axial offset of the sealing element relative to the adapter is prevented in both directions.

Some exemplary embodiments also provide for connection between the cannula assembly and adapter to occur in a material-sealed manner, that is to provide cohesion between the connecting partners by atomic or molecular forces.

Before the adapter is placed on the receptacle and screwed on, the cannula assembly may be inserted into the adapter.

The proximal end of the adapter may be moreover equipped with an outside thread for firm connection with the receptacle. It is especially useful if this outside thread is designed as a (female) part of a Luer-Lock connection to facilitate connection with a (male) part of a Luer-Lock connection of the receptacle, which has a respective inside thread.

In this manner, the adapter can be used to connect a cannula with the receptacle and to thereby seal the distal opening of the receptacle. An advantage is found in that the adapter can be used with a large number of receptacles which are available on the market, in particular syringes, syringe bodies, cartridges or injection devices which are equipped with a (male) Luer-Lock connection with inside thread.

It is also possible to provide the adapter with other thread designs and to use it in this manner with receptacles which are equipped with threads that are not consistent with the Luer-Lock principle.

For connection and closure, the adapter—which may be with an already inserted cannula assembly—can be placed onto the Luer-Lock connection of the receptacle and can be screwed on with one rotary motion. The limit stop in the passage opening may be designed such that, with a screwed on closure system, the sealing element in the intended end position is pressed with predetermined axial and/or radial contact pressure against the tip of the receptacle, which causes the desired sealing effect, thereby sealing the through-channel of the receptacle against the cannula.

For sealing the cannula itself which, in some embodiments in an assembled position protrudes from the adapter at the distal end, a further protection is provided in securing and sealing this end of the cannula in order to achieve the required sterile long term storage capability.

According to the present invention therefore, an attachable closure cap is moreover provided which, for example, can include a hard outside region and a sealing elastomer inside region. The closure cap can be placed on the distal end of the adapter and can thereby surround the protruding part of cannula at least partially with the sealing elastomer inside region, thereby sealing it. In some embodiments, the adapter is therefore equipped at its distal end with an extension for attaching and holding a closure cap.

In some embodiments, the pre-fillable or prefilled container thus includes a closure cap which is designed to—in an attached position—seal the channel of the cannula relative to the environment in order to ensure the stable and sterile long term storage capability. When attaching the sealing cap, the cannula can, for example, be slid into the sealing elastomer material in the inside region of the sealing cap, so that the elastomer material exerts a slight pressure in axial and/or radial direction onto the opening of the cannula when the closure cap is attached, thereby closing the cannula.

The adapter and the cannula assembly can also be manufactured and stored together as an assembly group and can then be connected with the receptacle. In this manner, they represent a closure system for the receptacle which can be flexibly configured, for example, with different cannulas. In one exemplary design, this closure system can already include the aforementioned closure cap.

Some exemplary embodiments provide that the adapter and/or the closure cap are provided with a certain color scheme, which is selected subject to at least one characteristic of the cannula, such as subject to the outside diameter, the inside diameter, the length and/or the type of the bevel grind of the cannula.

A color system is, for example, established in Standard EN ISO 6009, which determines a color subject to the gauge size of the cannula. In this manner, the color of the adapter and/or the color of the closure cap can be especially used to provide a user direct information in regard to the outside diameter of the cannula. Safety and access time can thereby be improved.

In some embodiments, the color of the adapter and/or the closure cap conforms to the color coding according to Standard ISO 6009 in order to give the user information in regard to the outside diameter of the cannula and thus the gauge size. In this way, a user of a pre-fillable or prefilled container can quickly receive information in regard to the cannula properties and can easily and reliably select the required container for a specific application.

Combined color systems are also possible. For example, a first color assignment for the adapter to provide the user with information regarding the outside diameter or respectively the gauge size of the installed cannula and a second color assignment for the closure cap which, for example, provides information in regard to the type of bevel grind or the length of the cannula.

The closure system provided according to the present invention—which may be provided with an already inserted cannula assembly—can be used with a pre-fillable or pre-filled container for storage and to apply a fluid, in particular a pharmaceutical or cosmetic preparation, in order to seal the through-channel of the receptacle and to attach a cannula.

In this manner, a pre-fillable or prefilled container, in particular a pre-fillable or prefilled syringe, a pre-fillable or prefilled syringe body, a pre-fillable or prefilled cartridge or a pre-fillable or prefilled injection device can very be easily provided, "ready to use" for storage and/or to apply a fluid, in particular a pharmaceutical or cosmetic preparation.

Receptacles, suitable according to the present invention, therefore include a plurality of syringes, syringe bodies, cartridges or injection devices which are available on the market and which may be equipped with a (male) Luer-Lock connection with inside thread.

One advantage provided according to the present invention is that these receptacles can be manufactured cost effectively in high numbers without having to provide a suitable cannula already during manufacturing of the container and attach it to same.

Since such receptacles are often manufactured from a synthetic material and are produced in the injection molding process, production thereof is greatly simplified. Moreover, handling during production is clearly easier since no receptacles with attached cannula have to be processed.

Moreover, it is also far easier to provide a great variety in regard to container size and cannula, without expensive storage being necessary. This is due to the fact that according to the present invention, receptacle and cannula can be manufactured, stored, and transported, and connected with each other according to the intended use, independently from one another.

Thus, receptacles having a volume, for example, of 0.25 mL, 0.5 mL, 0.6 mL, 1.0 mL, 1.2 mL, 1.5 mL, 2.0 mL, 2.25 mL, 3.0 mL, 5.0 mL, 10 mL, 20 mL or 50 mL can be very easily combined with cannulas of various gauge sizes, for example 27 G, 28 G, 29 G, 30 G and in particular with cannulas having very small outside diameters with gauge sizes 31 G, 32 G, 33 G, or 34 G.

In addition to the storage, the costs for tools can also be reduced since the containers can be manufactured independently from the dimensions of the cannulas.

Containers which are suitable according to the present invention can be manufactured as a single component from a transparent material, such as glass or a synthetic material. The synthetic material can include a thermoplastic or thermosetting synthetic material.

It is also possible to manufacture the receptacle from more than one material, as described, for example, in document DE 10 2014 211 018 A1, which is incorporated in its entirety herein by reference. The herein described embodiment of a receptacle for pharmaceutical preparations makes it possible to make use of the very good inert properties of glass in contact with other substances, and at the same time to make a connection with a Luer-Lock connection possible, where a connecting body is provided consisting of a synthetic material.

The thermoplastic synthetic materials can include the synthetic materials commonly used and permissible in the medical sector, consequently the thermoplastic synthetic material can be or can include a cyclo-olefin-copolymer (COC), cyclo-olefin-polymer (COP), acrylonitrile-butadiene-styrene (ABS), polyamide (PA), poly-lactate (PLA), polymethylmethacrylate (PMMA), polycarbonate (PC) or polyethylene-terephthalate (PET).

Suitable thermosetting synthetic materials which are commonly used and permissible in the medical sector can include or can consist of a cellulose-acetate (CA) or a transparent thermosetting resin.

A suitable glass can be a borosilicate glass, which can have the following composition (in weight %):

| | |
|---|---|
| $SiO_2$ | 65% to 82% |
| $B_2O_3$ | 5% to 13% |
| $\Sigma\ Na_2O + K_2O$ | 4% to 10% |
| $Al_2O_3$ | 2% to 9% |
| $\Sigma\ CaO + MgO + BaO + SrO$ | 0% to 5%. |

Such a glass can have a composition (in weight %):

| | |
|---|---|
| $SiO_2$ | 73% to 79% |
| $B_2O_3$ | 9% bis 12% |
| $Na_2O$ | 5% to 8% |
| $K_2O$ | 0% to 0.5% |
| $Li_2O$ | 0% to 0.3% |
| $Al_2O_3$ | 3.5% to 7% |
| CaO | 0% to 3% |
| BaO | 0% to 1% |
| F | 0 to 0.3% |
| $\Sigma\ CaO + MgO + BaO + SrO$ | 0% to 3% |

In some embodiments, such a glass can have a composition (in weight %):

| | |
|---|---|
| $SiO_2$ | 71% to 77% |
| $B_2O_3$ | 9% to 12% |
| $Na_2O$ | 5.5% to 8.5% |
| $K_2O$ | 0.1% to 1.0% |
| $Li_2O$ | 0% to 0.3% |
| $Al_2O_3$ | 5.5% to 8% |
| CaO | 0% to 1.5% |
| BaO | 0% to 1% |
| F | 0 to 0.3% |
| $\Sigma\ CaO + MgO + BaO + SrO$ | 0% to 2% |

The pre-fillable or prefilled container may be further characterized in that, in an assembled position, the contact pressure of the sealing element, in particular onto the face side of the tip, is at least 0.1 to 30 N, such as 5 to 20 N. The pre-fillable container provided according to the present invention moreover may be characterized in that, in an assembled position, the contact pressure of the sealing element in the closure cap onto the end of the cannula is at least 20 N, such as at least 30 N.

Due to the interaction of both seals, a long term storage is also made possible in regard to the stability, and in the case of a sterilization of the container also for the sterility.

To further increase the sealing effect, the face-side sealing area can be designed alternatively or in addition with a central, truncated cone shaped protrusion and, in some embodiments, the truncated shaped protrusion of the sealing element interacts in the assembled position with the through-channel of the tip of the receptacle. In other words, the protrusion of the sealing element protrudes at least in sections into the through-channel of the receptacle which is to be sealed. Good sealing results can be achieved if the protrusion protrudes into the through-channel at least 0.1 mm, such as at least 1 mm or at least 2 mm, and not more than 5 mm, such as not more than 4 mm or not more than 3 mm.

The protrusion engaging into the through-channel leads to an additional advantage since it secures the sealing element in its position. A semicircular protrusion is possible and can be used essentially for centering in the through channel.

Exemplary embodiments provided according to the present invention therefore relate also to a prefilled container including a syringe, a syringe body, a cartridge, or an injection device, with a very thin cannula for injecting a fluid, for example a pharmaceutical or cosmetic preparation. The cosmetic preparation may, for example, include a cosmetic compound. With this, exemplary embodiments provided according to the present invention make it possible to connect a receptacle in a very simple manner with a cannula having a gauge size of greater than 30 G, such as 31 G, 32 G, 33 G, or 34 G.

The prefilled container can be filled with a fluid or with a liquid, for example with a pharmaceutical preparation or with a liquid cosmetic compound. According to the present invention, a container prefilled with a fluid or a liquid, such as with a cosmetic compound, can therefore also be provided which may be characterized in that a cannula 40 has a gauge size of greater than 30 G, such as 31 G, 32 G, 33 G or 34 G.

Exemplary embodiments disclosed herein provide herewith also a method, including for injecting or applying of a fluid, for example a pharmaceutical or cosmetic preparation from or with a prefilled "ready to use" container provided according to the present invention, wherein a cannula having a gauge size of greater than 30 G, such as 31 G, 32 G, 33 G, or 34 G, is used.

The present invention also provides a cosmetic process, including injecting or applying of a cosmetic compound by use of a pre-filled container provided according to the present invention. The chamber is filled with a liquid, such as a cosmetic compound, and the cannula has a gauge size of greater than 30 G, such as 31 G, 32 G, 33 G or 34 G.

The invention provides that a prefilled container provided according to the present invention, after having been filled, can be stored for at least one year, such as at least two years, at least three years, or even longer than three years, wherein the applicable sterilization requirements are adhered to.

It is herein advantageous if the previously discussed assemblies are resilient to X-ray or gamma radiation and are thus responsive to X-ray or gamma-ray sterilization, which eliminates microbial contamination in the pre-fillable or prefilled container.

In some exemplary embodiments, the previously described assemblies are temperature resilient to 121° C. and can consequently also be autoclaved.

Depending on the preparation, a filled, in particular a pre-filled container, can then also be sterilized together with the preparation. This can contribute considerably to an improved storage capability, since germs inside the container can generally be eliminated with high certainty.

To prevent, for example, manipulation of a pre-filled container which is equipped with the disclosed closure system, some exemplary embodiments provided according to the present invention equip the form-fit connection, in other words the Luer-Lock connection, that is created through engaging of at least two connecting partners with additional applications that counter an unintentional opening and reclosing and/or other manipulations.

In some embodiments, a covering in the form of sealing or a band can be provided which surround at least sections of the outside surface of the adapter and the outside surface of the container, connecting them with one another. The covering can be designed such that a turning movement of the adapter to open the container will damage the covering and can be seen by the user. It can thus be prevented that the container is opened by turning the closure system and is possibly reclosed. A container that was opened is thus easily recognized.

In another or supplementary exemplary embodiment, it is provided to further develop the Luer-Lock connection, which is separable by a turning motion, into a non-separable Luer-Lock connection. This can occur, for example, in that in addition to the Luer-Lock connection, a material-seal connection is created; that is to say, a connection due to cohesion between connecting partners by atomic or molecular forces, that is to say between closure system and container which may interact with the Luer Lock connection or supplements the same. For this purpose, a material-seal connecting point or a material-seal connecting surface between outside and inside thread can be created, for example, by application of an adhesive, through laser welding or by UV welding, wherein this additional connection then hardens when the container is closed.

The Luer-Lock connection can thus be converted surprisingly easily into a non-separable connection. Thus, it can be ensured that a container that is prefilled with a fluid, as well as the filled fluid, cannot be manipulated.

For better clarification of the present invention, drawings presenting exemplary embodiments provided according to the present invention are provided and described herein; however, the illustrated embodiments are not always drawn according to scale.

Figure 1:
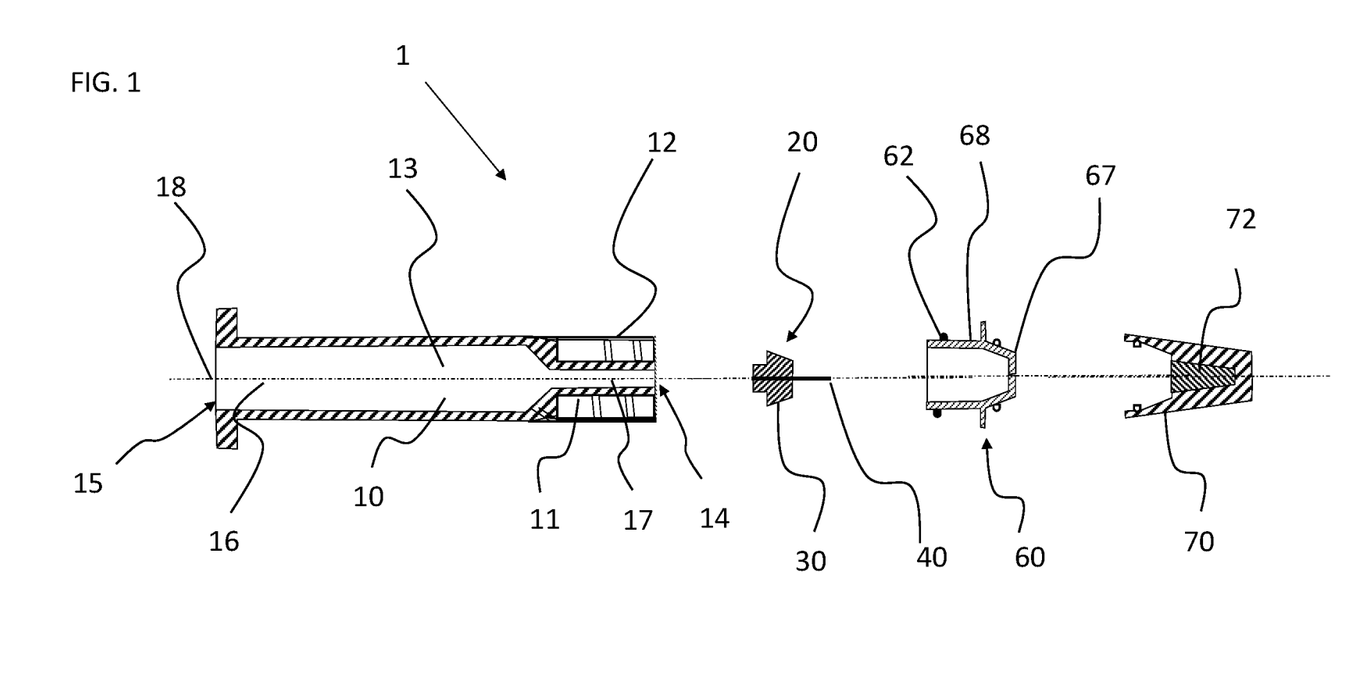
FIG. 1 is a sectional view of a receptacle, a cannula assembly, including a sealing element and a cannula, an adapter and a closure cap as essential components of an exemplary embodiment of a pre-fillable or prefilled container provided according to the present invention, where the sectional plane progresses approximately through the center of the previously referenced components and represents their center line.

Referring now to the drawings, FIG. 1 is a sectional view of one exemplary embodiment showing a receptacle 10, a cannula assembly 20, including a sealing element 30 and a cannula 40, an adapter 60 and a closure cap 70 as essential components of the pre-fillable or prefilled receptacle 1 for storage and/or application of a fluid, in particular a pharmaceutical or cosmetic preparation, provided according to the present invention.

Receptacle 10 in the illustrated embodiment, and without limitation to the illustrated embodiment, is a syringe with a Luer-Lock connection with inside thread and a chamber volume of 10 mL.

Collectively, a pre-fillable or prefilled container 1 for storage and/or application of a fluid, in particular a pharmaceutical or cosmetic preparation is disclosed, comprising a receptacle 10, in particular a syringe with a syringe body, a cartridge or an injection device with a chamber 13 to accommodate the fluid; moreover comprising a cannula assembly 20. The cannula assembly includes a cannula 40 and a sealing element 30 and the cannula assembly 20 is attachable to receptacle 10, as well as comprising a closure cap 70. An outside channel opening 43 of cannula 40 protrudes into a sealing, such as elastomer inside region 72 of closure cap 70, which seals channel opening 43. Due to a radial and/or axial compression of sealing element 30, as well as due to sealing of channel opening 43 by closure cap 70, chamber 13 is sealed in a fluid-tight manner.

Thus, the present invention discloses a size-flexible, cannula-flexible, preassembled, prefilled syringe with Luer-Lock, or, respectively, a stack needle with adapter, preassembled on the Luer-Lock with long term seal which—in a kind of modular design—renders all variants of cannulas, in particular the very thin ones (for example 31 G to 34 G) suitable for integration into the system.

According to the present invention, adapter 60 and cannula assembly 20 can be used with different receptacles 10, including with syringes, syringe bodies, cartridges or injection devices with different chamber volumes, such as in the range of 0.6 mL to 50 mL, and consisting of glass or a synthetic material. Receptacle 10 in the illustrated embodiment has a Luer-Lock connection with inside thread 11.

Cannula assembly 20 and adapter 60 serve to connect cannula 40 with receptacle 10 to make available pre-fillable or prefilled container 1 for storage and/or application of a fluid, for example a pharmaceutical or cosmetic preparation. Container 1 can be filled with the fluid, and the pre-filled container can be stored in advance of the fluid being administered by cannula 40. Receptacle 10 in the illustrated embodiment has a cylindrical longitudinal shape and has a central chamber 13 to accommodate the fluid. Chamber 13 is limited axially by a proximal end 15 and a distal end 14. During application, distal end 14 points in the direction to the person handling the device.

The descriptions "distal" and "proximal" are used analogously also for the additional components of container 1 and refer to the respective sides or directions of said components in an assembled position.

Proximal end 15 of chamber 13 includes an opening 16 into which a stopper can be inserted to move a filled fluid by a stopper movement, out of chamber 13 for instance via a piston rod, or hydraulically driven in an axial direction toward the opposite distal end 14. In a reverse movement, a fluid can be drawn into chamber 13.

For this purpose, distal end 14 of receptacle 10 is equipped with a through-channel 17, which is surrounded by a tip 12. Due to a respective stopper movement, a fluid (not illustrated) filled into chamber 13 can then be removed through said through-channel 17, or due to a reversed stopper movement a fluid can be drawn through said through-channel 17 into chamber 13. The dotted line identified with number 18 indicates the center axis of receptacle 10. It also indicates the reference axis for the additional components.

Figure 3:
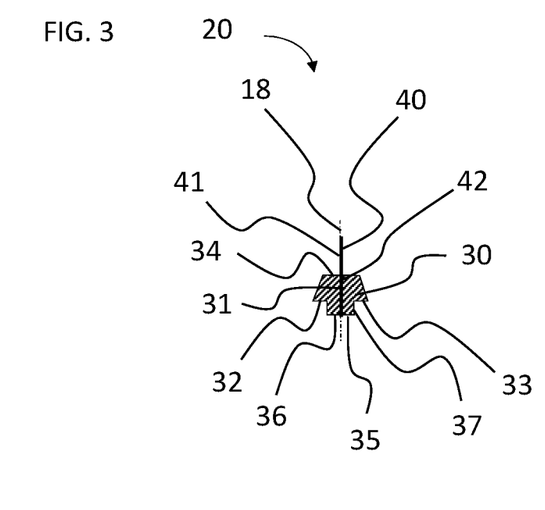
FIG. 3 is a sectional view of the cannula assembly in FIG. 2, where the sectional plane progresses approximately through the center of the cannula assembly and represents its center line.

Cannula assembly 20 represents an essential component provided according to the present invention and is shown schematically in an exemplary embodiment in a sectional view in FIG. 3.

Figure 2:
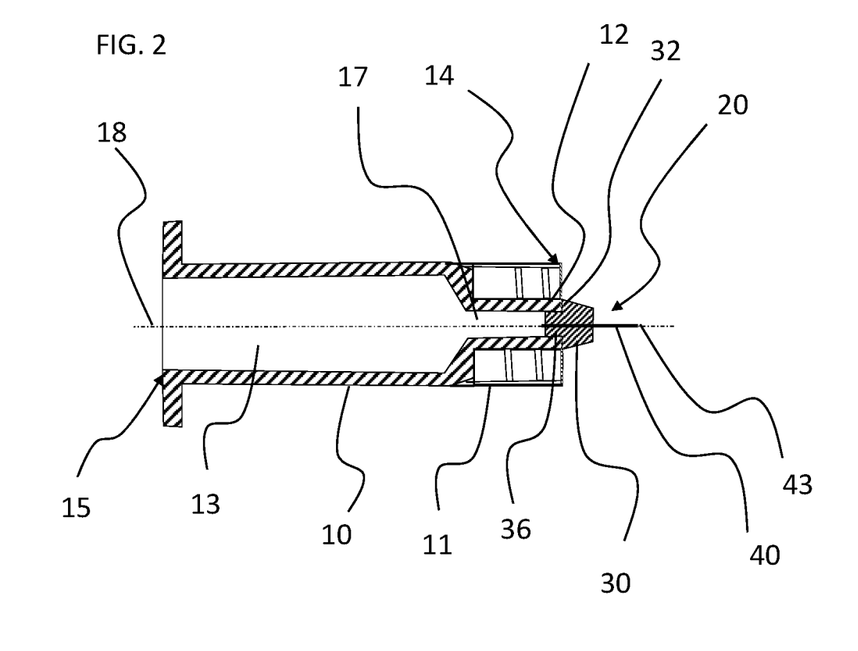
FIG. 2 is a sectional view of an exemplary embodiment of a receptacle with an attached cannula assembly, including a sealing element and a cannula, where the sectional plane progresses approximately through the center of these components and represents their center line.

FIG. 2 additionally shows a sectional view of a receptacle 10 with attached cannula assembly 20, including a sealing element 30 and a cannula 40. The cannula assembly, according to the embodiment illustrated in FIGS. 2 and 3, includes a cylinder-symmetrical sealing element 30 with an axial passage 31, and a cannula 40 with a through-channel 41. Cannula 40 is arranged coaxially relative to sealing element 30 and at least in sections inside passage 31. A section of outside surface area 42 of cannula 40 is connected firmly with sealing element 30 in a form-fitting and/or material-sealed manner. At least one face side 33 of sealing element 30 includes a circular region surrounding passage 31. The region forms a face-side sealing surface 32 in a plane vertical to center axis 18 of sealing element 30.

As previously outlined, a material sealed connection herein is understood to mean a cohesion of the connective partner elements by atomic or molecular forces. A form-fit connection indicates interlocking of at least two connective partners, in that they fit closely together where, due to the close fit, a fluid-tight seal is also provided.

Axial passage 31 of sealing element 30 serves to accommodate cannula 40; that is to say, a hollow needle or an injection needle with a through-channel 41, which can be used in the medical sector. The connection between sealing element 30 and cannula 40 is herein liquid and/or gas-tight in the sense of the present invention.

The present invention makes use of cannulas in sizes 27 G to 30 G, such as 31 G, 32 G, 33 G, and 34 G and greater, where possible. This is advantageous for a patient-friendly administering of a pharmaceutical preparation.

Due to the exceedingly small cannula diameter that can be used according to the present invention, a patient is now subjected to a greatly reduced pain sensation during an injection or drawing of bodily fluids. Injecting or applying a medical preparation in oral surgery, in particular injection of an anesthetic in the oral cavity of a patient, is herein advantageously supported, because the oral cavity is in particular known to be subject to increased pain sensation.

Also, injecting or applying a medical preparation in ophthalmology, in particular for suppression of eyelid reflexes or dilation of the pupils of a patient, is greatly supported because the small cannula diameter that can be used according to the present invention causes only very slight injuries or tissue damage which, based on experience, heal very quickly.

When injecting or applying a medical preparation in nephrology, in particular in the application of marker-substances for tracing fluid-dynamic processes, very small vessels can now be reached, and greater accuracy can also be achieved in robotically 3D-controlled application in the collection of fluid-dynamic processes.

The substantially same advantages occur also in injecting or applying a medical preparation in nuclear medicine, in the application of radioactive emitting isotopes, for example in the treatment of tumors, where active substances of a respective preparation can be administered locally and also quantitively metered more precisely and by causing lesser pain.

Injections or applications of cosmetic preparations, for example of hyaluronic acid or a BOTOX® (onabotulinumtoxinA) based preparation, are also less uncomfortable according to the present invention.

Use of a prefilled container, as disclosed herein, for sterile storage of a pharmaceutical or cosmetic preparation for a duration of more than one year, such as more than two years or more than three years, is hereby advantageously recommended.

In the illustrated embodiment, the cannula is shown only in size 34 G.

In an assembled position, cannula 40 is arranged in sealing element 30 in such a way that it completely penetrates sealing element 30. In the illustrated embodiment, the protrusion on the side with face-side sealing surface 32 is approximately 0.2 mm; a protrusion in the range of 0.1 mm to 3 mm, such as to 2 mm, is advantageous in order to prevent that the sealing element covers the inlet to the hollow needle.

In the illustrated embodiment, the protrusion on the opposite side is about 4 cm. A protrusion in a range of approximately 0.6 cm (⅖ inch) to approximately 5 cm (2 inch) is advantageous to create the necessary free space of cannula 40 relative to container 10 during use.

Sealing element 30 is manufactured from elastomer materials and comprises a thermoplastic elastomer, in particular butyl-, chloro-butyl-, bromo-butyl- or polyisoprene rubber. It is approved for use in contact with a pharmaceutical preparation.

To be able to provide a sufficiently wide sealing area between the face side of tip 12 and face-side sealing surface 32, face-side sealing surface 32 features an expansion in radial direction of approximately 0.8 mm, wherein an expansion of at least 0.5 mm, such as of at least 0.7 mm or of at least 1 mm is viewed as favorable.

To further improve the sealing effect and to also achieve a radial compression in addition to an axial compression during sealing, sealing surface 32 in the illustrated embodiment is provided with a central protrusion 36. This protrusion 36 is of a truncated cone-shaped design, which facilitates especially easy joining by self-aligning in the process of connecting cannula assembly 20 and receptacle 10 and in addition ensures uniform radial compression.

The radial compression—in particular in embodiments with a truncated cone-shaped protrusion 36—can be influenced by the pitch or respectively the angle between center axis 18 of the sealing element and the outside surface line of the truncated cone shaped protrusion. This may be at least 1°, such as at least 8° or at least 10° to 30°.

Central protrusion 36 engages in mounted position, at least in sections in through-channel 17, or respectively protrudes into same.

In this manner, an increase in the sealing effect between the opening of through channel 17 and sealing element 30 can be easily achieved. The additional advantage is provided that the seal between sealing element 30 and through-channel 17 occurs already in through-channel 17 itself, so that no fluid can get into the gap between the face sides of tip 12 and sealing element 30.

Figure 4:
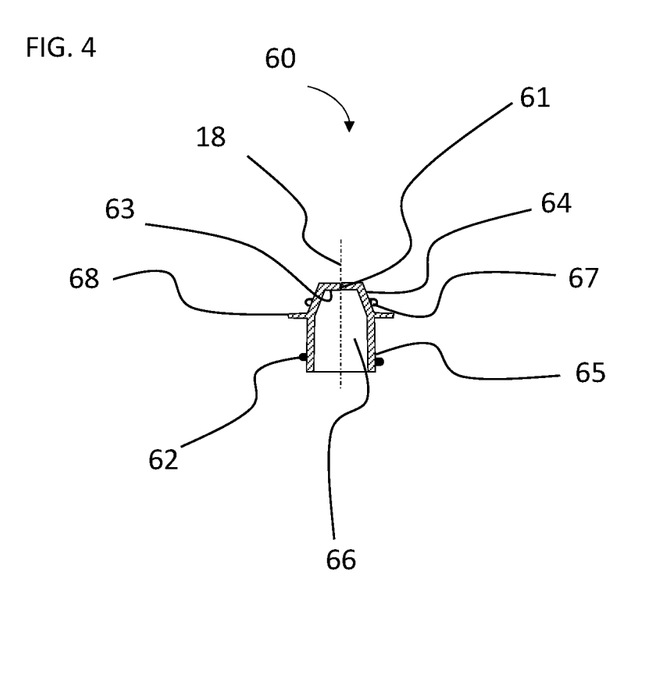
FIG. 4 is a sectional view of an exemplary embodiment of an adapter provided according to the present invention, where the sectional plane progresses approximately through the center of the adapter and represents its center line.

Cannula assembly 20 can be fitted to tip 12 of receptacle 10. Retention of cannula assembly 20 on tip 12 and generating the necessary compression in axial and/or radial direction occurs by adapter 60, which is shown in FIG. 4 in a sectional view of an exemplary embodiment.

Adapter 60 and cannula 20, together, can represent closure system 50 for receptacles 20 to produce a pre-fillable or prefilled container 1. A closure system 50 is shown in a sectional view in FIG. 5, comprising a cannula assembly provided according to the exemplary embodiment in FIG. 3 and an adapter provided according to the exemplary embodiment in FIG. 4. Closure system 50 in FIG. 5 moreover includes a closure cap 70, which is placed onto adapter 60 and held.

Adapter 60 serves to connect cannula 40 with receptacle 10. It is designed in the embodiment of an elongated hollow body with an axial passage opening 61, one proximal end 65 and one distal end 64. The inside diameter of passage opening 61 is expanded at proximal end 65 and represents a retainer 66 for holding sealing element 30, and moreover proximal end 15 includes an outside thread 62 as part of a Luer-Lock connection which is, or can be, connected with inside thread 11 of the receptacle 10. "Elongated" is herein understood such that adapter 60, at least according to the following cited standards, in direction of center line 18 has the length of a Luer-Lock outside thread or of a Luer-Lock also referred to as a female connection.

Outside thread 62 of adapter 60 is designed as a (female) part of a Luer-Lock connection and complies with respective Standards ISO 11040, ISO 80369-1, or ISO 80369-7.

Retainer 66 is adapted geometrically to the outside geometry of sealing element 30 of cannula assembly 20, which has to be accommodated and thus makes it possible to slide sealing element 30 at least partially, originating from the face side axially into adapter 60 until a limit stop 63, which is formed by the transition of the passage opening with the expanded inside diameter to the passage opening with the smaller inside diameter, and which thereby prevents further insertion of sealing element 30. In the illustrated embodiment, retainer 66 is designed conically tapering consistent with the outside contour of sealing element 30. This makes it possible to slide sealing element 30 with low force axially into retainer 66 and to center it radially in retainer 66.

Adapter 60 in the illustrated embodiment also has an extension 67 which makes it possible to place closure cap 70 on distal end 64 and to hold it in the intended position. Closure cap 70 is designed to—in an assembled position—protect the part of cannula 40 protruding relative to adapter 60 and to close outside channel opening 43 of channel 41 of cannula 40 tightly in the sense of the present invention, in other words liquid and/or fluid tight.

Adapter 60 in the illustrated embodiment moreover has a mounting ring 68 in the embodiment of a hexagon ring. This supports handling and simplifies for the user mounting at or on receptacle 10.

Figure 5:
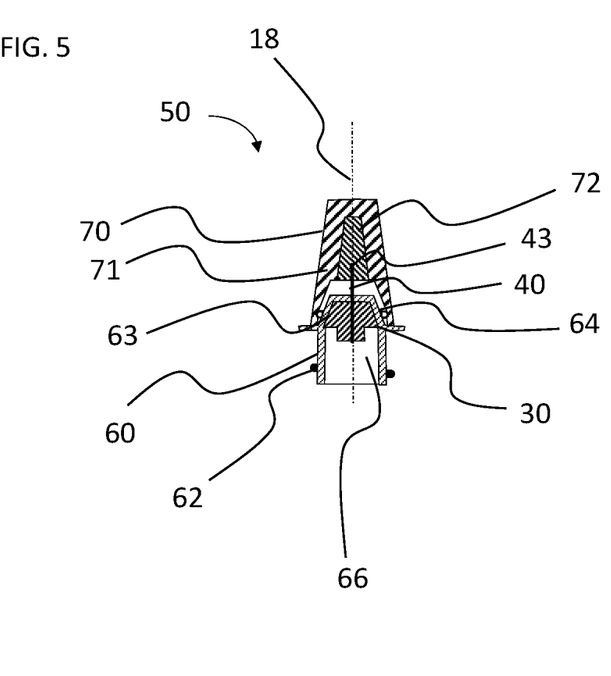
FIG. 5 is a sectional view of a closure system, including a cannula assembly provided according to FIG. 3 and an adapter according provided to FIG. 4 and a closure cap, where the sectional plane progresses approximately through the center of these components and represents their center line.

In the exemplary embodiment illustrated in FIG. 5, cannula assembly 20 is inserted up to the intended position into adapter 60. In the illustrated embodiment, closure cap 70, which is placed on adapter 60 and held by extension 67, has a hard outside region 71 and a sealing elastomer inside region 72. The part of cannula 40 protruding relative to adapter 60 protrudes at least in sections into elastomer inside region 72 of closure cap 70. In order to ensure reliable sealing, cannula 40 should protrude—in an assembled position—at least 2 mm, such as at least 3 mm or 4 mm or more, into elastomer inside region 72. In this case, elastomer material 72 exerts a slight pressure in axial and/or radial direction onto cannula opening 43 of cannula 40 when closure cap 70 is attached and closes same tightly in the sense of the present invention.

The seal makes it possible to seal channel 41 of cannula 40 relative to the environment in a liquid and/or gas tight manner. In this way, the stable and sterile long term storage capability can also be ensured.

Figure 6:
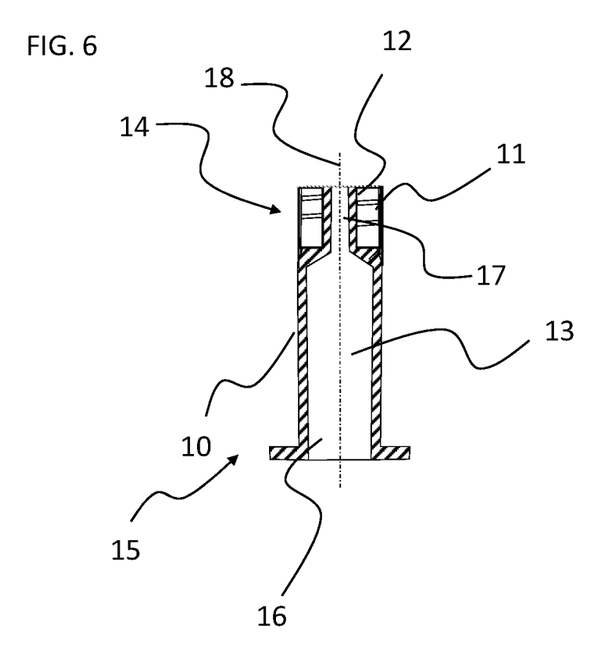
FIG. 6 is a sectional view of a receptacle in the embodiment of a syringe, where the sectional plane progresses approximately through the center of the receptacle and represents its center line.

FIG. 6 shows a sectional view of an exemplary embodiment of a syringe as a receptacle 10 suitable according to the present invention. Receptacle 10 in this example consists of a transparent material, for example of thermoplastic synthetic material cyclo-olefin-polymer (COP). Other material, for example thermosetting materials or glass, are also considered for receptacle 10.

Suitable thermoplastic materials include a cyclo-olefin-copolymer (COC), cyclo-olefin-polymer (COP), acrylonitrile-butadiene-styrene (ABS), polyamide (PA), poly-lactate (PLA), polymethylmethacrylate (PMMA), polycarbonate (PC) or polyethylene-terephthalate (PET).

Suitable thermosetting synthetic materials include a cellulose-acetate (CA) or a transparent thermosetting resin.

Suitable glasses comprise a borosilicate glass, which may have a composition (in weight %) of:

$SiO_2$ 65% to 82%
$B_2O_3$ 5% to 13%
$\Sigma Na_2O+K_2O$ 4% to 10%
$Al_2O_3$ 2% to 9%
$\Sigma CaO+MgO+BaO+SrO$ 0% to 5%

Figure 7:
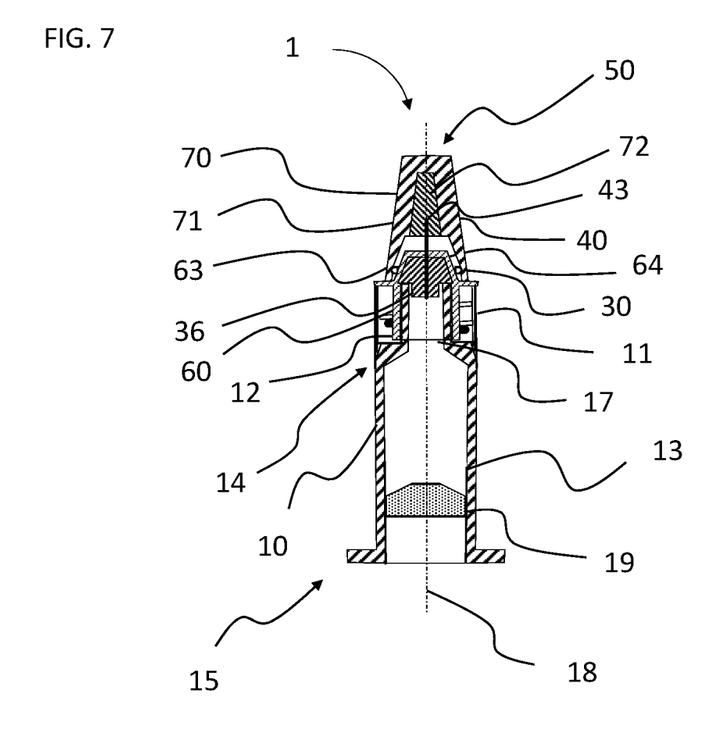
FIG. 7 is a sectional view of an exemplary embodiment of a pre-fillable container provided according to the present invention, including a receptacle as illustrated in FIG. 6 and a closure system as illustrated in FIG. 5, where the sectional plane progresses approximately through the center of the receptacle and represents its center line.

FIG. 7 shows another sectional view of a pre-fillable container 1 for storage and/or application of a fluid, for example a pharmaceutical or cosmetic preparation.

Pre-fillable container 1 provided according to the present invention includes a receptacle 10—a syringe in the example in FIG. 2 or 6—and an attached closure system 50, as shown in FIG. 5, with a cannula assembly 20 provided according to the exemplary embodiment in FIG. 3, and an adapter 60 provided according to the exemplary embodiment in FIG. 4.

Simply as an example, a stopper 19 is shown which closes opening 16 at proximal end 15 of the receptacle. A fluid, for example a pharmaceutical or cosmetic preparation, can be filled into chamber 13.

Closure system 50 and receptacle 10 are connected with one another by a Luer-Lock connection. In an assembled position, cannula 40 is in fluid-contact with chamber 13 of the receptacle. Adapter 60 makes it possible to connect a cannula 40, such as a cannula having a gauge size greater than 30 G, such as 31 G, 32 G, 33 G, or 34 G, firmly and permanently tightly with receptacle 10.

A contact pressure of sealing element 30 onto the face side of tip 12 of at least 0.1 to 30 N, such as 5 to 20 N, is produced in assembled position by closure system 50.

The present invention allows connection of a receptacle 10 in an especially simple manner, thereby providing the pre-fillable or prefilled container 1.

In the case of pre-filled container 1, chamber 13 is filled at least partially with a fluid. The fluid can comprise a pharmaceutical preparation or also a liquid cosmetic preparation.

According to the present invention, a prefilled container 1 with a liquid, such as a cosmetic preparation, can also be provided. The container may be characterized in that cannula 40 has a gauge size of greater than 30 G, such as 31 G, 32 G, 33 G, or 34 G.

The present invention moreover provides a cosmetic process, comprising injecting or applying a cosmetic preparation by using prefilled container 1, where chamber 13 is filled with a liquid, such as with a cosmetic preparation, and cannula 40 has a gauge size greater than 30 G, such as 31 G, 32 G, 33 G, or 34 G.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

COMPONENT IDENTIFICATION LISTING 1 pre-Tillable or prefilled container
10 receptacle
11 Luer-Lock inside thread
12 tip
13 chamber
14 distal end
15 proximal end
16 opening
17 through-channel
18 center axis
19 stopper
20 cannula assembly
30 sealing element
31 passage
32 face side sealing surface
33 face side
34 distal end
35 proximal end
36 protrusion
37 outside surface line
40 cannula
41 channel
42 outside surface
43 cannula opening
50 closure system
60 adapter
61 passage opening
62 outside thread
63 limit stop
64 distal end
65 proximal end
66 retainer
67 extension
68 mounting ring
70 closure cap
71 outside region
72 elastomer inside region

What is claimed is:

1. A pre-fillable or prefilled container for at least one of storage or application of a fluid, the pre-fillable or prefilled container comprising:
a receptacle comprising a chamber for accommodation of the fluid;
a cannula assembly comprising a cannula and a sealing element, the cannula comprising an outside channel opening, the cannula assembly being attachable to the receptacle, the sealing element comprising at least one face side which, in a mounted position, faces the receptacle and comprises a passage surrounded by an annular region which forms a face-side sealing surface in a plane perpendicular to a center axis of the sealing element, the cannula terminating flush with the sealing element on at least one of the at least one face side which, in the mounted position, faces the chamber; and
a closure cap comprising a sealing, wherein the channel opening of the cannula protrudes into the sealing of the closure cap thus sealing the channel opening, wherein due to at least one of a radial compression or an axial compression of the sealing element, as well as due to sealing of the channel opening by the closure cap, the chamber is sealed in a fluid-tight manner.

2. The pre-fillable or prefilled container of claim 1, wherein the receptacle comprises a body having a proximal end and a distal end, wherein the distal end has an axial through-channel with a tip surrounding the through-channel, wherein the distal end has an inside thread as part of a Luer-Lock connection, wherein the sealing element comprises a symmetric sealing element with the passage, wherein the passage is an axial passage, wherein the cannula is arranged coaxially relative to the sealing element and at least in sections inside the axial passage of the sealing element, wherein one section of an outside surface area of the cannula is connected firmly with the sealing element in at least one of a material seal or a form fitting manner, the pre-fillable or prefilled container further comprising an adapter configured to connect the cannula assembly with the tip of the receptacle, wherein the adapter is in the form of an elongated hollow body with an axial passage opening, a proximal end, and a distal end, wherein an inside diameter of the passage opening is expanded at the proximal end of the adapter and represents a retainer configured to hold the sealing element, wherein the proximal end of the adapter includes an outside thread which is connected with or connectable with the inside thread of the receptacle, wherein, in the mounted position, the cannula assembly is inserted into the retainer and seals the through-channel when the adapter is connected with the receptacle, and wherein, in the mounted position, the cannula communicates with the chamber.

3. The pre-fillable or prefilled container of claim 2, wherein, in the mounted position, a contact pressure of the sealing element onto a face side of the tip is at least 0.1 N to 30 N.

4. The pre-fillable or prefilled container of claim 2, wherein at least one of:
the cannula protrudes relative to the sealing element approximately 0.1 mm to 3 mm on a side of the face-side sealing surface; or
the cannula has a protrusion relative to the sealing element on an opposite side of the sealing element within a range of approximately 0.6 cm to approximately 5 cm.

5. The pre-fillable or prefilled container of claim 2, wherein the face-side sealing surface comprises a truncated cone shaped protrusion which surrounds the central passage and which engages at least in sections with the through-channel or protrudes into the through-channel.

6. The pre-fillable or prefilled container of claim 5, wherein an angle between the center axis and an outside surface line of the truncated cone shaped protrusion is at least 1°.

7. The pre-fillable or prefilled container of claim 2, wherein the adapter comprises an extension at its distal end that is configured to attach and hold the closure cap.

8. The pre-fillable or prefilled container of claim 1, wherein the receptacle is fabricated from a transparent material.

9. The pre-fillable or prefilled container of claim 8, wherein the transparent material comprises a thermoplastic synthetic material comprising or consisting of a cyclo-olefin-copolymer (COC), a cyclo-olefin-polymer (COP), acrylonitrile-butadiene-styrene (ABS), polyamide (PA), poly-lactate (PLA), polymethylmethacrylate (PMMA), polycarbonate (PC) or polyethylene-terephthalate (PET).

10. The pre-fillable or prefilled container of claim 8, wherein the transparent material comprises a thermosetting synthetic material comprising or consisting of a cellulose-acetate (CA) or a thermosetting resin.

11. The pre-fillable or prefilled container of claim 8, wherein the transparent material comprises a borosilicate glass having the following composition (in weight %):
$SiO_2$ 65% to 82%;
$B_2O_3$ 5% to 13%;
$\Sigma Na_2O+K_2O$ 4% to 10%;
$Al_2O_3$ 2% to 9%; and
$\Sigma CaO+MgO+BaO+SrO$ 0% to 5%.

12. The pre-fillable or prefilled container of claim 1, wherein the cannula has a gauge size of 27 G to 34 G.

13. The pre-fillable or prefilled container of claim 1, further comprising at least one of a liquid or a fluid at least partially filling the receptacle, wherein the cannula has a gauge size of greater than 30 G.

14. The pre-fillable or prefilled container of claim 1, wherein the receptacle is a syringe with a syringe body.

15. A closure system for connecting with a receptacle, the closure system comprising:
a cannula assembly, comprising:
a cylindrically symmetric sealing element with an axial passage; and
a cannula arranged coaxially relative to the sealing element and at least in sections inside the axial passage of the sealing element, wherein one section of an outside surface area of the cannula is connected firmly with the sealing element in at least one of a material seal or a form fitting manner and wherein at least one face side of the sealing element includes a circular region surrounding the passage, the region forming a face-side sealing surface in a plane vertical to a center axis of the sealing element, wherein the cannula terminates flush with the sealing element on at least one of the at least one face side which, in a mounted position, is configured to face a chamber of the receptacle.

16. The closure system of claim 15, further comprising:
an adapter in the form of a longitudinal hollow body with an axial passage opening, a proximal end, and a distal end, wherein an inside diameter of the passage opening is expanded at the proximal end and represents a retainer configured to hold the sealing element of the cannula assembly, the proximal end including an outside thread as part of a Luer-Lock connection.

17. The closure system of claim 16, further comprising a closure cap which has a hard outside region and a sealing elastomer inside region which is placed on the distal end of the adapter.

18. The closure system of claim 16, wherein the closure system is configured to connect to a syringe, a syringe body, or a cartridge.

19. A method of treating a patient, the method comprising:
injecting or applying a medical preparation to the patient, the medical preparation being held in a container, the container comprising:
a receptacle comprising a chamber for accommodation of the medical preparation;
a cannula assembly comprising a cannula and a sealing element, the cannula comprising an outside channel opening, the cannula assembly being attachable to the receptacle, the sealing element comprising at least one face side which, in a mounted position, faces the receptacle and comprises a passage surrounded by an annular region which forms a face-side sealing surface in a plane perpendicular to a center axis of the sealing element, the cannula terminating flush with the sealing element on at least one of the at least one face side which, in the mounted position, faces the chamber; and
a closure cap comprising a sealing, wherein the channel opening of the cannula protrudes into the sealing of the closure cap thus sealing the channel opening, wherein due to at least one of a radial compression or an axial compression of the sealing element, as well as due to sealing of the channel opening by the closure cap, the chamber is sealed in a fluid-tight manner.

20. The method of claim 19, wherein the injecting or applying comprises at least one of:
- injecting or applying the medical preparation in oral surgery;
- injecting the medical preparation in an oral cavity of the patient, the medical preparation comprising an anesthetic;
- injecting or applying the medical preparation in ophthalmology for suppression of eyelid reflexes or dilation of the pupils of the patient;
- injecting or applying the medical preparation in nephrology in the application of marker-substances for tracing fluid-dynamic processes;
- injecting or applying the medical preparation in nuclear medicine in the application of radioactive emitting isotopes; or
- injecting or applying the medical preparation in the form of a cosmetic preparation comprising hyaluronic acid or a onabotulinumtoxinA based preparation.

* * * * *

UNITED STATES PATENT AND TRADEMARK OFFICE
CERTIFICATE OF CORRECTION

Page 1 of 1

PATENT NO. : 11,865,319 B2
APPLICATION NO. : 16/899953
DATED : January 9, 2024
INVENTOR(S) : Tom Van Ginneken It is certified that error appears in the above-identified patent and that said Letters Patent is hereby corrected as shown below:

In the Specification

Column 3
At Line 63, please delete "pre-Tillable", and substitute therefore --pre-fillable--.

Column 4
At Line 7, please delete "pre-Tillable", and substitute therefore --pre-fillable--.

Signed and Sealed this
Twenty-third Day of December, 2025

John A. Squires
*Director of the United States Patent and Trademark Office*